United States Patent
Van Der Laan et al.

(10) Patent No.: US 10,202,594 B2
(45) Date of Patent: Feb. 12, 2019

(54) PROLINE-SPECIFIC ENDOPROTEASE AND USE THEREOF

(71) Applicant: DSM IP ASSETS B.V., Heerlen (NL)

(72) Inventors: Jan Metske Van Der Laan, Echt (NL); Peter Jozef Ida Van De Vondervoort, Echt (NL); Chantal Christis, Echt (NL); Martine Spaans, Echt (NL); Angela De Bruine-Paulus, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 4 days.

(21) Appl. No.: 15/314,892

(22) PCT Filed: Jun. 3, 2015

(86) PCT No.: PCT/EP2015/062325
§ 371 (c)(1),
(2) Date: Nov. 29, 2016

(87) PCT Pub. No.: WO2015/185590
PCT Pub. Date: Dec. 10, 2015

(65) Prior Publication Data
US 2018/0119127 A1    May 3, 2018

(30) Foreign Application Priority Data

Jun. 3, 2014   (EP) .................................... 14170879
Jun. 17, 2014  (EP) .................................... 14172644

(51) Int. Cl.
   *C12N 9/50*      (2006.01)
   *C12N 9/62*      (2006.01)
(52) U.S. Cl.
   CPC ........ *C12N 9/62* (2013.01); *C12Y 304/21026* (2013.01)
(58) Field of Classification Search
   CPC ..................................................... A61K 38/00
   USPC ......................................................... 435/219
   See application file for complete search history.

(56) References Cited

U.S. PATENT DOCUMENTS

2017/0081651 A1 * 3/2017 Van Der Laan .......... A23L 2/84
2017/0198272 A1 * 7/2017 Van Der Laan .......... C12N 9/62

FOREIGN PATENT DOCUMENTS

WO         03/104382 A1    12/2003
WO      2012/174127 A1    12/2012

OTHER PUBLICATIONS

International Search Report and International Patent Application of PCT/EP2015/062325 dated Sep. 29, 2015.
Kang, Chao et al., "Gene cloning and enzymatic characterization of an endoprotease Endo-Pro-Aspergillus niger" Journal of Industrial Microbiology and Biotechnology, May 18, 2013, pp. 855-664, vol. 40, vol. 8, Basingstoke, GB.

* cited by examiner

*Primary Examiner* — Tekchand Saidha
(74) *Attorney, Agent, or Firm* — McBee Moore Woodward & Vanik IP, LLC; Susan McBee; Chester Moore

(57) ABSTRACT

The present invention relates to a polypeptide having proline-specific endoprotease activity, wherein the polypeptide has less than 70% residual activity when the polypeptide has been kept at a temperature of 65° C. for 15 min.
The invention further relates to a polypeptide having proline-specific endoprotease activity comprising an amino acid sequence according to SEQ ID NO: 1, wherein SEQ ID NO: 1 comprises at least one combination of amino acid substitutions selected from the group consisting of a combination selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), (T281S, L373I), (P304A, P469A), and (P466T, P469Q), a nucleic acid encoding a polypeptide having proline-specific endoprotease activity, a method of making a variant polypeptide having proline-specific endoprotease activity, a recombinant host cell and a method of producing the polypeptide and a process for the preparation of a food or feed product wherein the polypeptide is used.

19 Claims, 1 Drawing Sheet
Specification includes a Sequence Listing.

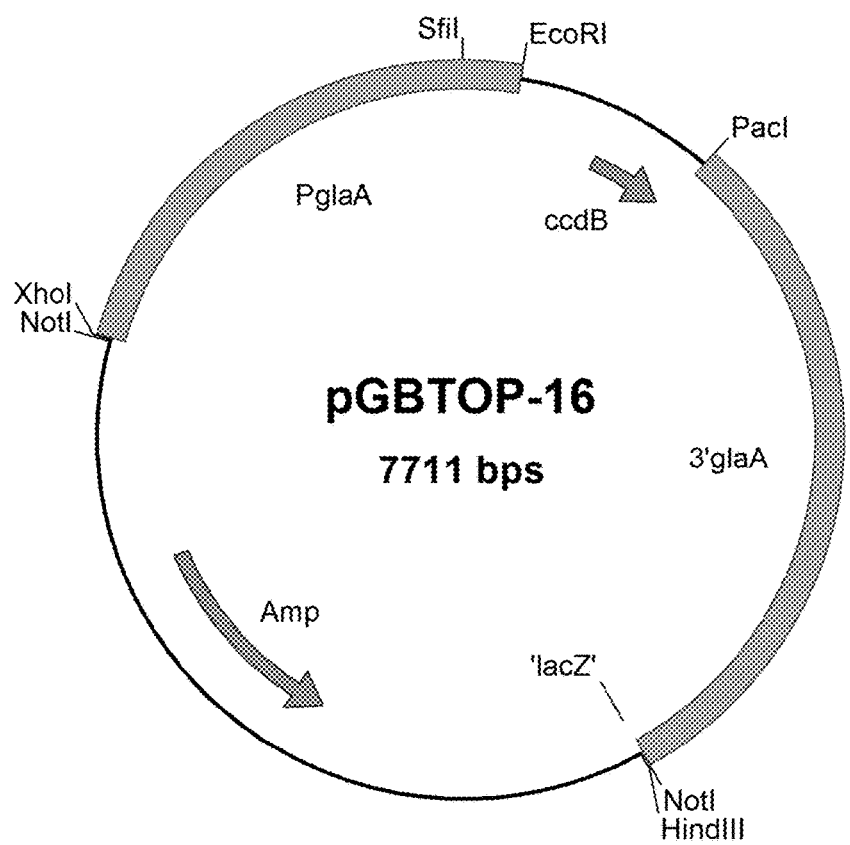

SEQUENCE LISTING

```
<160> NUMBER OF SEQ ID NOS: 8

<210> SEQ ID NO 1
<211> LENGTH: 521
<212> TYPE: PRT
<213> ORGANISM: Artificial Sequence
<220> FEATURE:
<223> OTHER INFORMATION: A. niger proline-specific endoprotease, with
      Pectinemethylesterase signal sequence

<400> SEQUENCE: 1

Met Val Lys Ser Ile Leu Ala Ser Val Phe Phe Ala Ala Thr Ala Leu
1               5                   10                  15

Ala Ala Arg Pro Arg Leu Val Pro Lys Pro Val Ser Arg Pro Ala Ser
            20                  25                  30

Ser Lys Ser Ala Ala Thr Thr Gly Glu Ala Tyr Phe Glu Gln Leu Leu
        35                  40                  45

Asp His His Asn Pro Glu Lys Gly Thr Phe Ser Gln Arg Tyr Trp Trp
    50                  55                  60

Ser Thr Glu Tyr Trp Gly Gly Pro Gly Ser Pro Val Val Leu Phe Thr
65                  70                  75                  80

Pro Gly Glu Val Ser Ala Asp Gly Tyr Glu Gly Tyr Leu Thr Asn Glu
                85                  90                  95

Thr Leu Thr Gly Val Tyr Ala Gln Glu Ile Gln Gly Ala Val Ile Leu
            100                 105                 110
```

```
Ile Glu His Arg Tyr Trp Gly Asp Ser Ser Pro Tyr Glu Val Leu Asn
            115                 120                 125

Ala Glu Thr Leu Gln Tyr Leu Thr Leu Asp Gln Ala Ile Leu Asp Met
130                 135                 140

Thr Tyr Phe Ala Glu Thr Val Lys Leu Gln Phe Asp Asn Ser Thr Arg
145                 150                 155                 160

Ser Asn Ala Gln Asn Ala Pro Trp Val Met Val Gly Gly Ser Tyr Ser
                165                 170                 175

Gly Ala Leu Thr Ala Trp Thr Glu Ser Val Ala Pro Gly Thr Phe Trp
            180                 185                 190

Ala Tyr His Ala Thr Ser Ala Pro Val Glu Ala Ile Tyr Asp Tyr Trp
            195                 200                 205

Gln Tyr Phe Tyr Pro Ile Gln Gln Gly Met Ala Gln Asn Cys Ser Lys
210                 215                 220

Asp Val Ser Leu Val Ala Glu Tyr Val Asp Lys Ile Gly Lys Asn Gly
225                 230                 235                 240

Thr Ala Lys Glu Gln Gln Ala Leu Lys Glu Leu Phe Gly Leu Gly Ala
                245                 250                 255

Val Glu His Phe Asp Asp Phe Ala Ala Val Leu Pro Asn Gly Pro Tyr
            260                 265                 270

Leu Trp Gln Asp Asn Asp Phe Ala Thr Gly Tyr Ser Ser Phe Phe Gln
            275                 280                 285

Phe Cys Asp Ala Val Glu Gly Val Glu Ala Gly Ala Ala Val Thr Pro
            290                 295                 300

Gly Pro Glu Gly Val Gly Leu Glu Lys Ala Leu Ala Asn Tyr Ala Asn
305                 310                 315                 320

Trp Phe Asn Ser Thr Ile Leu Pro Asp Tyr Cys Ala Ser Tyr Gly Tyr
                325                 330                 335

Trp Thr Asp Glu Trp Ser Val Ala Cys Phe Asp Ser Tyr Asn Ala Ser
            340                 345                 350

Ser Pro Ile Tyr Thr Asp Thr Ser Val Gly Asn Ala Val Asp Arg Gln
            355                 360                 365

Trp Glu Trp Phe Leu Cys Asn Glu Pro Phe Phe Tyr Trp Gln Asp Gly
            370                 375                 380

Ala Pro Glu Gly Thr Ser Thr Ile Val Pro Arg Leu Val Ser Ala Ser
385                 390                 395                 400

Tyr Trp Gln Arg Gln Cys Pro Leu Tyr Phe Pro Glu Thr Asn Gly Tyr
                405                 410                 415

Thr Tyr Gly Ser Ala Lys Gly Lys Asn Ala Ala Thr Val Asn Ser Trp
            420                 425                 430

Thr Gly Gly Trp Asp Met Thr Arg Asn Thr Thr Arg Leu Ile Trp Thr
            435                 440                 445

Asn Gly Gln Tyr Asp Pro Trp Arg Asp Ser Gly Val Ser Ser Thr Phe
450                 455                 460

Arg Pro Gly Gly Pro Leu Ala Ser Thr Ala Asn Glu Pro Val Gln Ile
465                 470                 475                 480

Ile Pro Gly Gly Phe His Cys Ser Asp Leu Tyr Met Ala Asp Tyr Tyr
                485                 490                 495

Ala Asn Glu Gly Val Lys Lys Val Asp Asn Glu Val Lys Gln Ile
            500                 505                 510

Lys Glu Trp Val Glu Tyr Tyr Ala
            515                 520
```

<210> SEQ ID NO 2
<211> LENGTH: 1566
<212> TYPE: DNA
<213> ORGANISM: Artificial Sequence
<220> FEATURE:
<223> OTHER INFORMATION: A. niger proline-specific endoprotease, with
      Pectinemethylesterase signal sequence

<400> SEQUENCE: 2

| | | | | | |
|---|---|---|---|---|---|
| atggtcaagt | ccatcctggc | ctccgtcttc | ttcgctgcca | ctgctcttgc | tgcaaggcct | 60 |
| cgtctcgttc | ccaagcccgt | ttctcgtccc | gccagctcca | agtccgctgc | tactactggt | 120 |
| gaggcctact | tgaacagct | gttggaccac | cacaaccctg | agaagggtac | tttctcgcaa | 180 |
| agatactggt | ggagcaccga | gtactggggt | ggtcccggat | cccccgttgt | cctgttcact | 240 |
| cccggtgagg | tcagcgctga | tggctacgag | ggttatctga | ccaacgagac | tctcaccggt | 300 |
| gtctacgccc | aggagattca | gggtgctgtc | atcctgatcg | aacaccgata | ctggggtgac | 360 |
| tcgtctccct | acgaggtgct | gaacgccgag | actctccagt | acttgaccct | cgaccaggct | 420 |
| atccttgata | tgacctactt | cgccgaaacc | gtcaagctcc | agtttgacaa | ctccacccgc | 480 |
| tccaacgctc | agaacgctcc | ttgggttatg | tcggcggca | gctacagcgg | tgctctgact | 540 |
| gcttggaccg | agtccgttgc | tcccggcacc | ttctgggctt | accacgccac | ctctgctcct | 600 |
| gttgaggcca | tctacgacta | ctggcaatac | ttctacccca | ttcagcaggg | tatggctcag | 660 |
| aactgctcca | agatgtctc | tcttgtagca | gaatacgtcg | acaagatcgg | caagaacggc | 720 |
| actgccaagg | agcaacaggc | tctgaaggag | cttttcggcc | taggagcagt | ggagcacttc | 780 |
| gacgacttcg | ccgctgttct | gcccaacggt | ccttacctct | ggcaagacaa | cgactttgcc | 840 |
| accggttact | cttctttctt | ccagttctgt | gatgccgtcg | agggtgtcga | ggctggtgct | 900 |
| gccgtcaccc | ccggtcctga | aggtgttggt | ctggaaaagg | cccttgctaa | ctacgcgaac | 960 |
| tggttcaact | ctaccatcct | ccccgattac | tgcgccagct | acggctactg | gactgacgag | 1020 |
| tggtccgtcg | cctgcttcga | ctcctacaac | gcctcctctc | ctatatacac | cgacaccagc | 1080 |
| gttggtaacg | ccgtcgaccg | tcagtgggag | tggttcctct | gcaatgagcc | cttctttttac | 1140 |
| tggcaggacg | gtgccccga | gggtacttca | acgatagtac | cccgcttagt | gtccgcctcc | 1200 |
| tactggcagc | gtcaatgtcc | gttgtacttc | cccgagacta | acggttacac | ctacggctcc | 1260 |
| gccaagggaa | agaacgccgc | caccgtcaac | agctggaccg | gtggctggga | catgacccgt | 1320 |
| aacaccaccc | gtctgatctg | gacgaacggc | caatacgacc | cctggcgtga | ctccggtgtc | 1380 |
| tcttccacct | tccgccccgg | tggtcccctc | gcttcgaccg | ccaacgagcc | cgtccagata | 1440 |
| atacccggtg | gtttccattg | ctccgacctc | tacatggcag | actactacgc | caacgagggc | 1500 |
| gtcaagaagg | ttgtcgacaa | cgaagtcaaa | caaatcaagg | agtgggttga | ggaatactac | 1560 |
| gcgtaa | | | | | | 1566 |

<210> SEQ ID NO 3
<211> LENGTH: 104
<212> TYPE: PRT
<213> ORGANISM: Artificial Sequence
<220> FEATURE:
<223> OTHER INFORMATION: Amino acid sequence horse heart cytochrome C

<400> SEQUENCE: 3

Gly Asp Val Glu Lys Gly Lys Lys Ile Phe Val Gln Lys Cys Ala Gln
1               5                   10                  15

Cys His Thr Val Glu Lys Gly Gly Lys His Lys Thr Gly Pro Asn Leu

```
                20                  25                  30

His Gly Leu Phe Gly Arg Lys Thr Gly Gln Ala Pro Gly Phe Thr Tyr
            35                  40                  45

Thr Asp Ala Asn Lys Asn Lys Gly Ile Thr Trp Lys Glu Glu Thr Leu
50                  55                  60

Met Glu Tyr Leu Glu Asn Pro Lys Lys Tyr Ile Pro Gly Thr Lys Met
65                  70                  75                  80

Ile Phe Ala Gly Ile Lys Lys Lys Thr Glu Arg Glu Asp Leu Ile Ala
                85                  90                  95

Tyr Leu Lys Lys Ala Thr Asn Glu
            100

<210> SEQ ID NO 4
<211> LENGTH: 30
<212> TYPE: PRT
<213> ORGANISM: Artificial Sequence
<220> FEATURE:
<223> OTHER INFORMATION: Fragment of cytochrome C digested with PEP

<400> SEQUENCE: 4

Gly Asp Val Glu Lys Gly Lys Lys Ile Phe Val Gln Lys Cys Ala Gln
1               5                   10                  15

Cys His Thr Val Glu Lys Gly Gly Lys His Lys Thr Gly Pro
            20                  25                  30

<210> SEQ ID NO 5
<211> LENGTH: 14
<212> TYPE: PRT
<213> ORGANISM: Artificial Sequence
<220> FEATURE:
<223> OTHER INFORMATION: Fragment of cytochrome C digested with PEP

<400> SEQUENCE: 5

Asn Leu His Gly Leu Phe Gly Arg Lys Thr Gly Gln Ala Pro
1               5                   10

<210> SEQ ID NO 6
<211> LENGTH: 32
<212> TYPE: PRT
<213> ORGANISM: Artificial Sequence
<220> FEATURE:
<223> OTHER INFORMATION: Fragment of cytochrome C digested with PEP

<400> SEQUENCE: 6

Gly Phe Thr Tyr Thr Asp Ala Asn Lys Asn Lys Gly Ile Thr Trp Lys
1               5                   10                  15

Glu Glu Thr Leu Met Glu Tyr Leu Glu Asn Pro Lys Lys Tyr Ile Pro
            20                  25                  30

<210> SEQ ID NO 7
<211> LENGTH: 7
<212> TYPE: PRT
<213> ORGANISM: Artificial Sequence
<220> FEATURE:
<223> OTHER INFORMATION: Fragment of cytochrome C digested with PEP

<400> SEQUENCE: 7

Gly Thr Lys Met Ile Phe Ala
1               5

<210> SEQ ID NO 8
<211> LENGTH: 21
<212> TYPE: PRT
```

```
<213> ORGANISM: Artificial Sequence
<220> FEATURE:
<223> OTHER INFORMATION: Fragment of cytochrome C digested with PEP

<400> SEQUENCE: 8

Gly Ile Lys Lys Lys Thr Glu Arg Glu Asp Leu Ile Ala Tyr Leu Lys
1               5                   10                  15

Lys Ala Thr Asn Glu
            20
```

PROLINE-SPECIFIC ENDOPROTEASE AND USE THEREOF

CROSS-REFERENCE TO RELATED APPLICATIONS

This application is a National Stage entry of International Application No. PCT/EP2015/062325, filed Jun. 3, 2015, which claims priority to European Patent Application No. 14170879.2, filed Jun. 3, 2014 and European Patent Application No. 14172644.8, filed Jun. 17, 2014. The disclosures of the priority applications are incorporated in their entirety herein by reference.

BACKGROUND

Field of the Invention

The present invention relates to a polypeptide having proline-specific endoprotease activity, a composition comprising the polypeptide, a nucleic acid encoding a proline-specific endoprotease, an expression vector comprising the nucleic acid encoding a proline-specific endoprotease, a recombinant host cell, a method for preparing proline-specific endoprotease and a process for preparing a food or feed product wherein the proline-specific endoprotease is used.

Description of Related Art

Proline-specific endoproteases are enzymes that hydrolyse a protein or peptide at a position where there is a proline in the protein or peptide.

A proline-specific endoprotease may for instance be derived from *Aspergillus niger* or *Penicillium chrysogenum*, such as disclosed in WO2002/046381 and WO2009/144269 respectively.

Other proline-specific endoprotease are known from WO2012/174127. WO2012/174127 discloses proline-specific protease from *Botryotini fuckeliana, Aspergillus clavatus, Sclerotinia sclerotiotum, Mycosphaerelly graminicola, Neuropspora crasse, Talaromyces stipitatus* and *Gibberella zeae*.

Proline-specific endoprotease can be used in several applications, for instance in the degradation of gluten (see for instance WO2005/027953 or WO2003/068170). Gluten is the insoluble protein fraction of cereals like wheat, rye, oat and barley. Gluten is a complex mixture of glutenin- and prolamine molecules which are thought to cause toxic effects, for instance in patients suffering from celiac disease. Celiac Sprue or celiac disease is considered to be an autoimmune disease. Patients suffering from Celiac Sprue need to follow a strict gluten-free diet, which is very difficult to follow because gluten is so widely used. The use of proline-specific endoprotease as a medicament or dietary supplement may alleviate the need for a strict gluten free diet (WO2003/068170).

Proline-specific endoproteases are also used for reducing haze in beer, wherein the proline-specific protease may be added during several stages of a beer production process (WO 2002/046381).

It is desirable that enzymes in food and feed applications have a suitable pH optimum and preferably are not active in the final food or beverage.

The aim of the present invention is an alternative proline-specific endoprotease with improved characteristics.

SUMMARY

In one aspect the present invention relates to a polypeptide having proline-specific endoprotease activity, wherein the polypeptide has less than 70% residual activity on acetyl-AlaAlaPro-paranitroaniline (Ac-AAP-pNA) as a substrate after the polypeptide has been kept at a temperature of 65° C. for 15 min. The residual activity of a polypeptide having proline-specific endoprotease activity is advantageously determined using acetyl-AlaAlaPro-paranitroaniline (Ac-AAP-pNA) as a substrate at a temperature of 20° C. and at a pH 4.5, for instance in a buffer at pH 4.5, for instance a sodium-acetate (NaAc) buffer, which may comprise a further salt such as NaCl. The residual activity may be determined by incubating a polypeptide as disclosed herein at a temperature of 20° C., and at a pH 4.5 for 60 min.

In another aspect, the present invention relates to a polypeptide having proline-specific endoprotease activity wherein the polypeptide is selected from the group consisting of a polypeptide having proline-specific endoprotease activity, optionally having less than 50% residual activity after the polypeptide has been kept at a temperature of 65° C. for 15 min, wherein the polypeptide is selected form the group consisting of:

i. a polypeptide, which, when aligned with an amino acid sequence according to SEQ ID NO: 1, comprises at least one combination of amino acids corresponding to combination selected from the group consisting of (Glu (E) at position 238, Val (V) at position 204, Ala (A) at position 460), (Ser (S) at position 279, Val (V) at position 242, Ile (I) at position 507), (Thr (T) at position 145, Met (M) at position 424), (Ala (A) at position 359, Ser (S) at position 379), (Ile (I) at position 170, Thr (T) at position 421), (Ser (S) at position 441, Ser (S) at position 484), (His (H) at position 470, Arg (R) at position 288), (His (H) at position 470, Gly (G) at position 387), (Ser (S) at position 281, Ile (I) at position 373), (Ala at position 304, Ala at position 469), and (Thr (T) at position 466, Gln (Q) at position 469), wherein the positions are defined with reference to SEQ ID NO: 1;

ii. a polypeptide comprising an amino acid sequence according to SEQ ID NO: 1, wherein SEQ ID NO: 1 comprises at least one combination of amino acid substitutions selected from the group consisting of the combinations (K238E, I204V, V460A), (F279S, A242V, N507I), (T145A, K424M), (T359A, F379S), (M170I, A421T), (N441S, G484S), (L470H, Q288R), (L470H, E387G), (T281S, L373I), (P304A, P469A), and (P466T, P469Q), wherein the substitutions are defined with reference to SEQ ID NO: 1;

iii. a polypeptide according to i) to iii), but lacking a signal sequence and/or a proprotein sequence;

iv. a polypeptide according to i) to iv) which has at least 60%, 70%, 75%, 80 85%, 90%, 91%, 92%, 93%, 94%, 95%, 96%, 97%, 98%, 99% or 100% identity to the amino acid sequence of SEQ ID NO: 1;

v. a polypeptide encoded by a nucleic acid which has at least 60%, 70%, 75%, 80%, 85%, 90%, 91%, 92%, 93%, 94%, 95%, 96%, 97%, 98%, 99% or 100% identity to SEQ ID NO: 2, or to a mature coding sequence of SEQ ID NO: 2, wherein SEQ ID NO: 2 comprises at least one mutation encoding at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), (T281S, L373I), (P304A, P469A), and (P466T, P469Q), wherein the amino acid substitutions are defined with reference to SEQ ID NO: 1.

The invention also provides a composition comprising a polypeptide having proline-specific endoprotease as disclosed herein.

In another aspect the present invention provides a method of generating a variant polypeptide having proline-specific endoprotease activity as disclosed herein.

The invention also provides a nucleic acid encoding a proline-specific endoprotease, which has at least 60%, 70%, 75%, 80%, 85%, 90%, 95%, 96%, 97%, 98%, 99%, or 100% sequence identity to SEQ ID NO: 2, or to a mature coding sequence of SEQ ID NO: 2, wherein SEQ ID NO: 2 comprises at least one a mutation encoding at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), (T281S, L373I), (P304A, P469A), and (P466T, P469Q), wherein the amino acid substitutions are defined with reference to SEQ ID NO: 1.

In another aspect the present invention relates to an expression vector comprising a polynucleotide encoding a polypeptide as disclosed herein.

In another aspect the present invention relates to a recombinant host cell comprising a polynucleotide sequence, or an expression vector as disclosed herein.

In yet another aspect the present invention relates to a method for the preparation of a polypeptide, comprising cultivating a host cell as disclosed herein under conditions that allow expression of the polypeptide, and preparing the polypeptide.

In another aspect the present invention relates to a process for the preparation of a food or feed product comprising incubating an intermediate form of the food or feed product with a polypeptide or a composition comprising a polypeptide as disclosed herein, and preparing the food product.

The present invention also relates to a food or feed product obtainable by a process as disclosed herein.

BRIEF DESCRIPTION OF THE DRAWINGS

FIG. 1 depicts an embodiment of the disclosure as described herein.

DETAILED DESCRIPTION OF A PREFERRED EMBODIMENT

Definitions

The term "baked products" is herein defined as any product prepared from a dough or a batter. The product may have a soft or a crisp character and may be of a white, light or dark type. Baked products include, but are not limited to, bread such as for instance white, whole-meal or rye bread, French baguette-type bread, laminated dough products such as (Danish) pastry, croissants or puff pastry, pita bread, tortillas, tacos, cakes, pancakes, biscuits, cookies, doughnuts, bagels, pie crusts, muffins, steamed bread, and crisp bread. Types of baked products, methods to characterize and to produce them are known to those skilled in the art see for example "Baking Science and Technology", by E. J. Pyler, L. A. Gorton, 2008, (2 volumes) Sosland Publishing Company, Kansas, USA, or "Baked Products: Science, Technology and Practice" by S. P. Cauvain, L. S. Young, 2006, Blackwell Publishing Ltd, Oxford, UK.

The term "complementary strand" can be used interchangeably with the term "complement". The complement of a nucleic acid strand can be the complement of a coding strand or the complement of a non-coding strand. When referring to double-stranded nucleic acids, the complement of a nucleic acid encoding a polypeptide refers to the complementary strand of the strand encoding the amino acid sequence or to any nucleic acid molecule containing the same.

The term "control sequence" can be used interchangeably with the term "expression-regulating nucleic acid sequence". The term as used herein refers to nucleic acid sequences necessary for and/or affecting the expression of an operably linked coding sequence in a particular host organism or in vitro. When two nucleic acid sequences are operably linked, they usually will be in the same orientation and also in the same reading frame. They usually will be essentially contiguous, although this may not be required. The expression-regulating nucleic acid sequences, such as inter alia appropriate transcription initiation, termination, promoter, leader, signal peptide, propeptide, prepropeptide, or enhancer sequences; Shine-Dalgarno sequence, repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either endogenous or heterologous to a host cell. Each control sequence may be native or foreign to the nucleic acid sequence encoding the polypeptide. When desired, the control sequence may be provided with linkers for the purpose of introducing specific restriction sites facilitating ligation of the control sequences with the coding region of the nucleic acid sequence encoding a polypeptide. Control sequences may be optimized to their specific purpose.

A "dairy product" refers to any kind of milk-based product intended to be used as food, feed or beverage, including but not limited to cheese, milk, skimmed milk, acidified milk, butter milk, condensed milk, spreads, margarines, yoghurt, ice cream, milk powder, butter, EMC (Enzyme Modified Cheese), dulce de leche, coffee whitener; coffee creamer, cream, ghee, dairy analogue, etcetera. Cheese may be any kind of cheese, e.g. fresh cheese, hard cheese, curd cheese, cream cheese, white mould cheese, blue mould cheese and process cheese. Examples of fresh cheese are Ricotta, Cream cheese, Neufchatel or Cottage cheese. Examples of hard cheese are Chester, Danbo, Manchego, Saint Paulin, Cheddar, Monterey, Colby, Edam, Gouda, Muenster, Swiss type, Gruyere, Emmenthaler, Parmigiano Reggiano, Grana Padano, Parmesan, Pecorino, Provolone, and Romano. Examples of curd cheese such as Feta cheese, Quotija cheese, pasta filata cheese such as Mozzarella, and Queso fresco cheese. Examples of cream cheese are Philadelphia cheese. Examples of white mould cheese are Brie and Camembert cheese. Examples of blue mould cheese are Gorgonzola and Danish blue cheese.

As used herein, the term "endogenous" refers to a nucleic acid or amino acid sequence naturally occurring in a host.

Endopeptidases or endoproteinases are able to break peptide bonds of nonterminal amino acids (i.e. within the protein), in contrast to exopeptidases, which break peptide bonds either from the amino or the carboxyl terminus. Endopeptidases do not tend to break down peptides into monomers, but result in relatively large peptide fragments. The specific generation of relatively large fragments is highly preferred in many food and feed related applications.

A particular case of endopeptidase is the oligopeptidase, whose substrates are oligopeptides instead of proteins The term "expression" includes any step involved in the production of the polypeptide including, but not limited to, transcription, post transcriptional modification, translation, post-translational modification, and secretion.

Polynucleotides of the present invention as described herein may be over-expressed in a host cell of the invention compared to a parent cell in which said gene is not over-expressed. Over-expression of a polynucleotide sequence is defined herein as the expression of the said sequence gene which results in an activity of the polypeptide encoded by the said sequence in a host cell being at least 1.1, at least 1.25 or at least 1.5-fold the activity of the polypeptide in the host cell; preferably the activity of said polypeptide is at least 2-fold, more preferably at least 3-fold, more preferably at least 4-fold, more preferably at least 5-fold, even more preferably at least 10-fold and most preferably at least 20-fold the activity of the polypeptide in the parent cell.

An expression vector comprises a polynucleotide coding for a polypeptide, such as a polypeptide according to the present invention, operably linked to the appropriate control sequences (such as a promoter, and transcriptional and translational stop signals) for expression and/or translation in vitro, or in a host cell of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e., a vector, which exists as an extra-chromosomal entity, the replication of which is independent of chromosomal replication, e.g., a plasmid, an extra-chromosomal element, a mini-chromosome, or an artificial chromosome. Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. The vector system may be a single vector or plasmid or two or more vectors or plasmids, which together contain the total DNA to be introduced into the genome of the host cell, or a transposon. A vector of the invention may comprise one, two or more, for example three, four or five polynucleotides of the invention, for example for overexpression.

The term "gene" as used herein refers to a segment of a nucleic acid molecule coding for a polypeptide chain, that may or may not include gene regulatory sequences preceding and following the coding sequence, e.g. promoters, enhancers, etc., as well as intervening sequences (introns) between individual coding segments (exons). It will further be appreciated that the definition of gene can include nucleic acids that do not encode polypeptide, but rather provide templates for transcription of functional RNA molecules such as tRNAs, rRNAs, etc.

A host cell as defined herein is an organism suitable for genetic manipulation and one which may be cultured at cell densities useful for industrial production of a target product, such as a polypeptide according to the present invention. A host cell may be a host cell found in nature or a host cell derived from a parent host cell after genetic manipulation or classical mutagenesis. Advantageously, a host cell is a recombinant host cell. A host cell may be a prokaryotic, archaebacterial or eukaryotic host cell. A prokaryotic host cell may be, but is not limited to, a bacterial host cell. An eukaryotic host cell may be, but is not limited to, a yeast, a fungus, an amoeba, an algae, a plant, an animal, or an insect host cell.

The term "heterologous" as used herein refers to nucleic acid or amino acid sequences not naturally occurring in a host cell. In other words, the nucleic acid or amino acid sequence is not identical to that naturally found in the host cell.

The term "hybridization" means the pairing of substantially complementary strands of oligomeric compounds, such as nucleic acid compounds. Hybridization may be performed under low, medium or high stringency conditions. Low stringency hybridization conditions comprise hybridizing in 6× sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency hybridization conditions comprise hybridizing in 6×SSC at about 45° C., followed by one or more washes in 0.2×SSC, 0.1% SDS at 60° C., and high stringency hybridization conditions comprise hybridizing in 6×SSC at about 45° C., followed by one or more washes in 0.2×SSC, 0.1% SDS at 65° C.

A nucleic acid or polynucleotide sequence is defined herein as a nucleotide polymer comprising at least 5 nucleotide or nucleic acid units. A nucleotide or nucleic acid refers to RNA and DNA. The terms "nucleic acid" and "polynucleotide sequence" are used interchangeably herein.

A "peptide" refers to a short chain of amino acid residues linked by a peptide (amide) bonds. The shortest peptide, a dipeptide, consists of 2 amino acids joined by single peptide bond.

The term "polypeptide" refers to a molecule comprising amino acid residues linked by peptide bonds and containing more than five amino acid residues. The term "protein" as used herein is synonymous with the term "polypeptide" and may also refer to two or more polypeptides. Thus, the terms "protein" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity in a presence of a specific substrate under certain conditions may be referred to as enzymes. It will be understood that, as a result of the degeneracy of the genetic code, a multitude of nucleotide sequences encoding a given polypeptide may be produced.

An "isolated nucleic acid fragment" is a nucleic acid fragment that is not naturally occurring as a fragment and would not be found in the natural state.

The term "isolated polypeptide" as used herein means a polypeptide that is removed from at least one component, e.g. other polypeptide material, with which it is naturally associated. The isolated polypeptide may be free of any other impurities. The isolated polypeptide may be at least 50% pure, e.g., at least 60% pure, at least 70% pure, at least 75% pure, at least 80% pure, at least 85% pure, at least 80% pure, at least 90% pure, or at least 95% pure, 96%, 97%, 98%, 99%, 99.5%, 99.9% as determined by SDS-PAGE or any other analytical method suitable for this purpose and known to the person skilled in the art. An isolated polypeptide may be produced by a recombinant host cell.

A "mature polypeptide" is defined herein as a polypeptide in its final form and is obtained after translation of a mRNA into polypeptide and post-translational modifications of said polypeptide. Post-translational modification include N-terminal processing, C-terminal truncation, glycosylation, phosphorylation and removal of leader sequences such as signal peptides, propeptides and/or prepropeptides by cleavage.

A "mature polypeptide coding sequence" means a polynucleotide that encodes a mature polypeptide.

The term "nucleic acid construct" is herein referred to as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" or "expression vector" when the nucleic acid construct contains all the control sequences required for expression of a coding sequence, wherein said control sequences are operably linked to said coding sequence.

A "proline-specific endoprotease" is a protease that hydrolyses a protein or peptide at a position where the protein or peptide contains a proline-residue. A proline-specific endoprotease may have proline-specific endopotease and/or proline-specific oligopeptidase activity (EC3.4.21.26). A proline-specific endoprotease is preferably an enzyme that hydrolyses a peptide bond at the carboxy-terminal end of proline residues, resulting in a peptide and/or polypeptide fragment with a C-terminal proline.

The term "promoter" is defined herein as a DNA sequence that binds RNA polymerase and directs the polymerase to the correct downstream transcriptional start site of a nucleic acid sequence to initiate transcription.

The term "recombinant" when used in reference to a cell, nucleic acid, protein or vector, indicates that the cell, nucleic acid, protein or vector, has been modified by the introduction of a heterologous nucleic acid, amino acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all. The term "recombinant" is synonymous with "genetically modified" and "transgenic".

"Sequence identity", or sequence homology are used interchangeable herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp276-277, at emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at www.ncbi.nlm.nih.gov.

The term "substantially pure" with regard to polypeptides refers to a polypeptide preparation which contains at the most 50% by weight of other polypeptide material. The polypeptides disclosed herein are preferably in a substantially pure form. In particular, it is preferred that the polypeptides disclosed herein are in "essentially pure form", i.e. that the polypeptide preparation is essentially free of other polypeptide material. Optionally, the polypeptide may also be essentially free of non-polypeptide material such as nucleic acids, lipids, media components, and the like. Herein, the term "substantially pure polypeptide" is synonymous with the terms "isolated polypeptide" and "polypeptide in isolated form". The term "substantially pure" with regard to polynucleotide refers to a polynucleotide preparation which contains at the most 50% by weight of other polynucleotide material. The polynucleotides disclosed herein are preferably in a substantially pure form. In particular, it is preferred that the polynucleotide disclosed herein are in "essentially pure form", i.e. that the polynucleotide preparation is essentially free of other polynucleotide material. Optionally, the polynucleotide may also be essentially free of non-polynucleotide material such as polypeptides, lipids, media components, and the like. Herein, the term "substantially pure polynucleotide" is synonymous with the terms "isolated polynucleotide" and "polynucleotide in isolated form".

A "substitution" as used herein in relation to polypeptides or nucleic acids, denotes the replacement of one or more amino acids in a polypeptide sequence or of one or more nucleotides in a polynucleotide sequence, respectively, by different amino acids or nucleotides, respectively. For instance, a substitution indicates that a position in a polypeptide as disclosed herein, such as a variant polypeptide, which corresponds to at least one position set out above in SEQ ID NO: 1, comprises an amino acid residue which does not appear at that position in the parent polypeptide (for instance the parent sequence SEQ ID NO: 1).

A "synthetic molecule", such as a synthetic nucleic acid or a synthetic polypeptide is produced by in vitro chemical or enzymatic synthesis. It includes, but is not limited to, variant nucleic acids made with optimal codon usage for host organisms of choice.

A synthetic nucleic acid may be optimized for codon use, preferably according to the methods described in WO2006/077258 and/or WO2008000632, which are herein incorporated by reference. WO2008/000632 addresses codon-pair optimization. Codon-pair optimization is a method wherein the nucleotide sequences encoding a polypeptide that have been modified with respect to their codon-usage, in particular the codon-pairs that are used, are optimized to obtain improved expression of the nucleotide sequence encoding the polypeptide and/or improved production of the encoded polypeptide. Codon pairs are defined as a set of two subsequent triplets (codons) in a coding sequence. Those skilled in the art will know that the codon usage needs to be adapted depending on the host species, possibly resulting in variants with significant homology deviation from SEQ ID NO: 2, but still encoding the polypeptide according to the invention.

As used herein, the terms "variant", "derivative", "mutant" or "homologue" can be used interchangeably. They can refer to either polypeptides or nucleic acids. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination approaches known to a skilled person in the art. Variant genes of nucleic acids may be synthesized artificially by known techniques in the art.

FIGURES

FIG. 1: pGBTOP-16 vector used for cloning of the GLA gene. The pGBTOP-16 vector is derived from the pGBTOP-12 vector described in WO 2011/009700. In addition to pGBTOP-12, it contains the ccdB gene from *E. coli* for positive selection for presence of an insert between the EcoRI and PacI cloning sites. The PacI restriction site replaces the SnaBI restriction site present in pGBTOP-12. This vector is linearized by NotI digestion prior to transformation.

SEQUENCES

SEQ ID NO: 1: Amino acid sequence of *Aspergillus niger* proline-specific endoprotease, containing a pectinemethylesterase signal sequence.

SEQ ID NO: 2: Nucleic acid sequence of *Aspergillus niger* proline-specific endoprotease, containing s pectinemethylesterase signal sequence.

SEQ ID NO:3 Amino acid sequence horse heart cytochrome C.

SEQ ID NO: 4: Fragment of cytochrome C digested with a PEP according to the present invention SEQ ID NO:5: Fragment of cytochrome C digested with a PEP according to the present invention SEQ ID NO: 6: Fragment of cytochrome C digested with a PEP according to the present invention SEQ ID NO:7: Fragment of cytochrome C digested with a PEP according to the present invention SEQ ID NO: 8: Fragment of cytochrome C digested with a PEP according to the present invention

DETAILED DESCRIPTION

In one aspect the present invention relates to a polypeptide having proline-specific endoprotease activity, wherein the polypeptide has less than 70% residual activity using acetyl-AlaAlaPro-paranitroaniline (Ac-AAP-pNA) as a substrate after the polypeptide has been kept at a temperature of 65° C. for 15 min. The residual proline-specific endoprotease activity is measured using acetyl-AlaAlaPro-paranitroaniline (Ac-AAP-pNA) at pH 4.5, for instance in a sodium-acetate buffer at pH 4.5 at 20 degrees Celsius. Surprisingly, a polypeptide that has less than 50% residual activity after the polypeptide has been kept at a temperature of 65° C. for 15 min can advantageously be used in applications such as in food or feed wherein no or little residual activity is desirable. Preferably, a polypeptide provided by the invention has less than 45%, 40%, 30%, 20%, 15%, 10%, such as less than 5% residual activity after the polypeptide has been kept at a temperature of 65° C. for 15 min. As defined herein less than 70%, 60%, 50%, or less than 45%, 40%, 30%, 20%, 15%, 10%, or 5%, residual activity means that the polypeptide exhibits less than 70%, 60%, 50%, or less than 45%, 40%, 30%, 20%, 15%, 10%, or 5% respectively, of the activity compared to the activity of the polypeptide before keeping the polypeptide at 65° C. for 15 min. Preferably, a polypeptide according to the present invention exhibits no residual activity after the polypeptide has been kept at a temperature of 65° C. for 15 min.

In one embodiment a polypeptide as disclosed herein is a polypeptide having proline-specific endoprotease activity, wherein the polypeptide has less than 90% residual activity using acetyl-AlaAlaPro-paranitroaniline (Ac-AAp-pNA) as a substrate after the polypeptide has been kept at a temperature of 60° C. for 15 min. The residual proline-specific endoprotease activity is measured using acetyl-AlaAlaPro-paranitroaniline (Ac-AAp-pNA) at pH 4.5, for instance in a sodium-acetate buffer at pH 4.5 at 20 degrees Celsius. Surprisingly, a polypeptide that has less than 70% residual activity after the polypeptide has been kept at a temperature of 60° C. for 15 min can advantageously be used in applications such as in food or feed wherein no or little residual activity is desirable. Preferably, a polypeptide provided herein has less than 80%, 70%, 60%, 50%, 40%, 30%, 20%, 15%, 10%, such as less than 5% residual activity after the polypeptide has been kept at a temperature of 60° C. for 15 min. As defined herein less than 70%, or less than 60%, 50%, 45%, 40%, 30%, 20%, 15%, 10%, or 5%, residual activity means that the polypeptide exhibits less than 70%, 60%, 50%, or less than 40%, 30%, 20%, 15%, 10%, or 5% respectively, of the activity compared to the activity of the polypeptide before keeping the polypeptide at 60° C. for 15 min. Preferably, a polypeptide according to the present invention exhibits no residual activity after the polypeptide has been kept at a temperature of 60° C. for 15 min.

The invention also provides a polypeptide having proline-specific endoprotease activity, optionally having less than 70% residual activity using acetyl-AlaAlaPro-paranitroaniline (Ac-AAp-pNA) as a substrate after the polypeptide has been kept at a temperature of 65° C. for 15 min, optionally having less than 90% residual activity using acetyl-AlaAlaPro-paranitroaniline (Ac-AAp-pNA) as a substrate after the polypeptide has been kept at a temperature of 60° C. for 15 min wherein the polypeptide is selected from the group consisting of i. comprises at least one combination of amino acids corresponding to combination selected from the group consisting of (Glu (E) at position 238, Val (V) at position 204, Ala (A) at position 460), (Ser (S) at position 279, Val (V) at position 242, Ile (I) at position 507), (Thr (T) at position 145, Met (M) at position 424), (Ala (A) at position 359, Ser (S) at position 379), (Ile (I) at position 170, Thr (T) at position 421), (Ser (S) at position 441, Ser (S) at position 484), (His (H) at position 470, Arg (R) at position 288), (His (H) at position 470, Gly (G) at position 387), (Ser (S) at position 281, Ile (I) at position 373), (Ala at position 304, Ala at position 469), and (Thr (T) at position 466, Gln (Q) at position 469), and optionally at least one further amino acid of Phe (F) at position 204, Asp (N) at position 205 or Ala (A) at position 477, wherein the polypeptide does not comprise amino acid Phe (F) at position 204, when the polypeptide comprises the amino acids Glu (E) at position 238, Val (V) at position 204, and Ala (A) at position 460, wherein the positions are defined with reference to SEQ ID NO: 1;

ii. a polypeptide comprising an amino acid sequence according to SEQ ID NO: 1, wherein SEQ ID NO: 1 comprises at least one combination of amino acid substitutions selected from the group consisting of the combinations (K238E, I204V, V460A), (F279S, A242V, N507I), (T145A, K424M), (T359A, F379S), (M170I, A421T), (N441S, G484S), (L470H, Q288R), (L470H, E387G), (T281S, L373I), (P304A, P469A), and (P466T, P469Q), and optionally at least one further amino acid substitution I204F, Y205N or P477A, wherein the amino acid substitution I204F is not present in a polypeptide having the amino acid substitutions K238E, I204V, and V460A wherein the substitutions are defined with reference to SEQ ID NO: 1;

iii. a polypeptide according to i) to iii), but lacking a signal sequence and/or a proprotein sequence;

iv. a polypeptide according to i) to iv), wherein the polypeptide has at least 60%, 70%, 75%, 80 85%, 90%, 91%, 92%, 93%, 94%, 95%, 96%, 97%, 98%, 99° or 100% identity to the amino acid sequence according to SEQ ID NO: 1;

v. a polypeptide encoded by a nucleic acid which has at least 60%, 70%, 75%, 80%, 85%, 90%, 91%, 92%, 93%, 94%, 95%, 96%, 97%, 98%, or 99% or 100% identity to SEQ ID NO: 2, or to a mature coding sequence of SEQ ID NO: 2, wherein SEQ ID NO: 2 comprises at least one mutation encoding at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), (I281S, L373I), (P304A, P469A), and (P466T, P469Q), and optionally at least one further amino acid substitution I204F, Y205N or P477A, wherein the amino acid substitution I204F is not present in a polypeptide having the amino acid substitutions K238E, I204V, and V460A, wherein the amino acid positions are defined with reference to SEQ ID NO: 1.

As used herein, when a polypeptide is aligned with a proline-specific endoprotease sequence of SEQ ID NO: 1, a polypeptide of the present invention will comprise at least one combination of amino acids selected from the group consisting of (Glu (E) at position 238, Val (V) at position 204, Ala (A) at position 460), (Ser (S) at position 279, Val (V) at position 242, Ile (I) at position 507), (Thr (T) at position 145, Met (M) at position 424), (Ala (A) at position 359, Ser (S) at position 379), (Ile (I) at position 170, Thr (T) at position 421), (Ser (S) at position 441, Ser (S) at position 484), (His (H) at position 470, Arg (R) at position 288), (His (H) at position 470, Gly (G) at position 387), (Ser (S) at position 281, Ile (I) at position 373), (Ala at position 304, Ala at position 469), and (Thr (T) at position 466, Gln (Q) at position 469), and optionally at least one further amino acid of Phe (F) at position 204, Asp (N) at position 205 or Ala (A) at position 477, wherein the polypeptide does not comprise amino acid Phe (F) at position 204, when the polypeptide comprises the amino acids Glu (E) at position 238, Val (V) at position 204, and Ala (A) at position 460, wherein the positions are defined with reference to SEQ ID NO: 1.

Those positions in a polypeptide of the invention, which may be a recombinant, synthetic or variant polypeptide, which correspond to the positions set out above in SEQ ID NO: 1 may be identified by aligning the sequence of the polypeptide of the present invention with that of SEQ ID NO: 1 using, for example, the alignment by the program Needle. The positions in the polypeptide of the present invention corresponding to the positions in SEQ ID NO: 1 as set out above may thus be identified and are referred to as those positions defined with reference to SEQ ID NO: 1.

The present invention also provides a polypeptide that is an isolated, substantially pure, pure, recombinant, synthetic or variant polypeptide of the polypeptide as disclosed herein.

Advantageously a polypeptide provided by the invention comprises at least one combination of amino acids corresponding to combination selected from the group consisting of (Glu (E) at position 238, Val (V) at position, Ala (A) at position 460), (Ser (S) at position 279, Val (V) at position 242, Ile (I) at position 507), (Thr (T) at position 145, Met (M) at position 424), (Ala (A) at position 359, Ser (S) at position 379), (Ile (I) at position 170, Thr (T) at position 421), (Ser (S) at position 441, Ser (S) at position 484), (His (H) at position 470, Arg (R) at position 288), (His (H) at position 470, Gly (G) at position 387), (Ser (S) at position 281, Ile (I) at position 373), (Ala at position 304, Ala at position 469), and (Thr (T) at position 466, Gln (Q) at position 469), and optionally at least one further amino acid of Phe (F) at position 204, Asp (N) at position 205 or Ala (A) at position 477, wherein the polypeptide does not comprise amino acid Phe (F) at position 204, when the polypeptide comprises the amino acids Glu (E) at position 238, Val (V) at position 204, and Ala (A) at position 460, wherein the positions are defined with reference to SEQ ID NO: 1.

In one embodiment, the invention provides a polypeptide having proline-specific endoprotease activity comprising an amino acid sequence according to SEQ ID NO: 1, wherein SEQ ID NO: 1 comprises at least one combination of amino acid substitutions selected from the group consisting of the combinations (K238E, I204V, V460A), (F279S, A242V, N507I), (T145A, K424M), (T359A, F379S), (M170I, A421T), (N441S, G484S), (L470H, Q288R), (L470H, E387G), (T281S, L373I), (P304A, P469A), (P466T, P469Q), (L470H, E387G, Y205N), (P466T, P469Q, I204F) and (P466T, P469Q, P477A), wherein the substitutions are defined with reference to SEQ ID NO: 1.

Preferably, the invention provides a polypeptide comprising at least one combination of amino acid substitutions as defined herein above, wherein the polypeptide has at least 60%, 70%, 75%, 80 85%, 90%, 91%, 92%, 93%, 94%, 95%, 96%, 97%, 98%, 99% or 100% identity to the amino acid sequence according to SEQ ID NO: 1. Accordingly, the present invention provides a polypeptide which has at least 60%, 70%, 75%, 80 85%, 90%, 91%, 92%, 93%, 94%, 95%, 96%, 97%, 98%, 99% or 100% identity to the amino acid sequence according to SEQ ID NO: 1 or to the mature polypeptide of SEQ ID NO: 1, wherein SEQ ID NO:1 comprises at least one combination of amino acid substitutions as defined herein above.

A polypeptide having proline-specific endoprotease activity which, when aligned with an amino acid sequence according to SEQ ID NO: 1 comprises at least one combination of amino acid substitutions as defined herein above, may comprise further substitutions, deletions and/or insertions at one or more further amino acid positions. For instance a polypeptide as disclosed herein may be a variant of the polypeptide or the mature polypeptide of SEQ ID NO:1 comprising a substitution, deletion or insertion at a position selected from the group consisting of (Glu (E) at position 238, Val (V) at position 204, Ala (A) at position 460), (Ser (S) at position 279, Val (V) at position 242, Ile (I) at position 507), (Thr (T) at position 145, Met (M) at position 424), (Ala (A) at position 359, Ser (S) at position 379), (Ile (I) at position 170, Thr (T) at position 421), (Ser (S) at position 441, Ser (S) at position 484), (His (H) at position 470, Arg (R) at position 288), (His (H) at position 470, Gly (G) at position 387), (Ser (S) at position 281, Ile (I) at position 373), (Ala at position 304, Ala at position 469), and (Thr (T) at position 466, Gln (Q) at position 469), and optionally at least one further amino acid of Phe (F) at position 204, Asp (N) at position 205 or Ala (A) at position 477, wherein the polypeptide does not comprise amino acid Phe (F) at position 204, when the polypeptide comprises the amino acids Glu (E) at position 238, Val (V) at position 204, and Ala (A) at position 460, as defined with reference to SEQ ID NO:1, and further having 1, 2, 3, 4, 5, 6, 7, 8, 9, 10, 11 or 12 or more further amino substitutions, deletions and/or insertions, whereby the polypeptide still has the activity or function of the polypeptide of the invention. The skilled person will appreciate that these minor amino acid changes in the polypeptide of the invention may be present (for example naturally occurring mutations) or made (for example using r-DNA technology) without loss of the protein function or activity. In case these mutations are present in a binding domain, active site, or other functional domain of the polypeptide a property of the polypeptide may change but the polypeptide may keep its activity. In case a mutation is present which is not close to the active site, binding domain, or other functional domain, less effect may be expected.

Functional equivalents of a polypeptide according to the invention can also be identified e.g. by screening combinatorial libraries of mutants, e.g. truncation mutants, of the polypeptide of the invention for the biological activity of the polypeptide of the invention. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g. for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477). The term "degenerate nucleic acid sequence" or "degenerate (oligo)nucleotide sequence" denotes a sequence of nucleic acids that includes one or more degenerate codons (as compared to a reference nucleic acid molecule that encodes a polypeptide). Degenerate codons contain different triplets of nucleic acids, but encode the same amino acid residue (i.e., GAU and GAC triplets each encode Asp). The codon degeneracy refers to the nature of the genetic code permitting variation of the nucleic acid sequence without affecting the aminoacid sequence of an encoded polypeptide. The skilled artisan is well aware of the "codon-bias" exhibited by a specific host cell in usage of nucleic acid codons to specify a given amino acid.

In addition, libraries of fragments of the coding sequence of a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3): 327-331).

A polypeptide provided by the invention may lack a signal sequence and/or a proprotein sequence. For instance a polypeptide as provided herein may be a polypeptide comprising an amino acid sequence according to SEQ ID NO: 1 comprising at least one combination of amino acid substitutions as defined herein above, and lacking the first 17 amino acids encoding of a signal sequence and/or lacking the following 19 amino acids encoding a prosequence. Accordingly a polypeptide provided by the invention may comprise a mature polypeptide of SEQ ID NO: 1, such as amino acid 37 to 521 of SEQ ID NO: 1 and comprising the at least one combination of amino acid substitutions as defined herein, wherein the amino acid methionine at position 1 in SEQ ID NO: 1 is counted as number 1.

A polypeptide provided by the invention may be encoded by any suitable nucleic acid such as a nucleic acid which has at least 60%, 70%, 75%, 80%, 85%, 90%, 91%, 92%, 93%, 94%, 95%, 96%, 97%, 98%, 99% or 100% identity to nucleic acid according to SEQ ID NO: 2, or to a mature coding sequence of SEQ ID NO: 2, wherein SEQ ID NO: 2 comprises at least one mutation encoding at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), (I281S, L373I), (P304A, P469A), and (P466T, P469Q), wherein the amino acid positions are defined with reference to SEQ ID NO: 1.

In one embodiment, a polypeptide encoded by a nucleic acid of SEQ ID NO: 2 or a mature coding sequence of SEQ ID NO: 2 as disclosed herein may be encoded by a nucleic acid sequence, which when aligned with SEQ ID NO: 2 comprises at least one further mutation encoding at least one further amino acid substitution I204F, Y205N or P477A, wherein the amino acid substitution I204F is not present in a polypeptide having the amino acid substitutions K238E, I204V, and V460A, and wherein the amino acid substitutions are defined with reference to SEQ ID NO: 1.

Typically, a polynucleotide sequence as disclosed herein is codon optimized, or a codon pair optimized sequence for optimal expression of a polypeptide as disclosed herein in a particular host cell.

In one embodiment the present invention features a biologically active fragment of a polypeptide as disclosed herein.

Biologically active fragments of a polypeptide of the invention include polypeptides comprising amino acid sequences sufficiently identical to or derived from the amino acid sequence of the proline-specific endoprotease protein (e.g. the mature amino acid sequence of SEQ ID NO:1), which include fewer amino acids than the full length protein but which exhibits at least one biological activity of the corresponding full-length protein. Typically, biologically active fragments comprise a domain or motif with at least one activity of the proline-specific endoprotease protein. A biologically active fragment may for instance comprise a catalytic domain. A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

The invention also features nucleic acid fragments which encode the above biologically active fragments of the proline-specific endoprotease protein.

A polypeptide according to the present invention may be a fusion protein. Techniques for producing fusion polypeptides are known in the art, and include ligating the coding sequences encoding the polypeptides so that they are in frame. Expression of the fused polypeptide is under control of the same promoter (s) and terminator. The hybrid polypeptides may comprise a combination of partial or complete polypeptide sequences obtained from at least two different polypeptides wherein one or more may be heterologous to a host cell. Such fusion polypeptides from at least two different polypeptides may comprise a binding domain from one polypeptide, operably linked to a catalytic domain from a second polypeptide. Examples of fusion polypeptides and signal sequence fusions are for example as described in WO2010/121933, WO2013/007820 and WO2013/007821.

A polypeptide according to the present invention may be derived from any suitable eukaryotic cell. A eukaryotic cell may be a mammalian, insect, plant, fungal, or algal cell. The wording "derived" or "derivable from" with respect to the origin of a polypeptide as disclosed herein, means that when carrying out a BLAST search with a polypeptide according to the present invention, the polypeptide according to the present invention may be derivable from a natural source, such as a microbial cell, of which an endogenous polypeptide shows the highest percentage homology or identity with the polypeptide as disclosed herein A polypeptide according to the present invention may be derived from a filamentous fungal cell or thermophilic filamentous fungal cell. Preferred filamentous fungal cells belong to a species of an *Acremonium, Aspergillus, Chrysosporium, Myceliophthora, Penicillium, Talaromyces, Rasamsonia, Thielavia, Fusarium* or *Trichoderma, Amorphotheca, Pseudocercosporella, Trametes, Rhizomucor, Calcarisporiella, Thermomyces, Thermoascus, Cornyascus, Myricoccum, Scytalidium, Chaetomium, Paecilomyces, Corynascus, Malbranchea, Stilbella, Thermomyces, Dactylomyces, Humicola, Chaetomium, Melanocarpus, Rhizomucor, Lentinula, Anaeromyces* genus, and most preferably belong to a species of *Aspergillus niger, Acremonium alabamense, Aspergillus awamori, Aspergillus foetidus, Aspergillus sojae, Aspergillus fumigatus, Talaromyces emersonii, Rasamsonia emersonii, Aspergillus oryzae, Chrysosporium lucknowense, Fusarium oxysporum, Myceliophthora thermophila, Trichoderma reesei, Thielavia terrestris, Penicillium chrysogenum, Amorphotheca resinae, Aureobasidium pullulans, Pseudocercosporella herpotrichoides, Trametes versicolor 52J, Rhizomucor pusillus, Calcarisporiella thermophila, Talaromyces thermophilus, Thermomyces lanuginosus, Thermoascus auratiacus, Cornyascus thermophilus, Myricoccum thermophilum, Scytalidium thermophilum, Myceliophthora hinnulea, Chaetomium thermophilum, Paecilomyces byssochlamydoides, Corynascus sepedonium, Malbranchea cinnamonmea, Thielavia australiensis, Stilbella thermophila, Thermomyces stellatus, Talaromyces emersonii, Dactylomyces thermophilus, Humicola hyalothermophilia, Acremonium thermophilum, Chaetomium olivicolor, Melanocarpus albomyces, Rhizomucor miehei, Lentinula edodes* or *Anaeromyces mucronatus*. A polypeptide according to the present invention may be derived from *Aspergillus niger, Aspergillus flavus, Aspergillus carbonarius, Aspergillus aculeatus, Rasamsonia emersonii*.

A polypeptide according to the present invention may be a naturally occurring polypeptide or a genetically modified or recombinant polypeptide.

A polypeptide as disclosed herein may be purified. Purification of protein is known to a skilled person in the art. A well-known method for purification of proteins is high performance liquid chromatography.

Polypeptides according to the present invention advantageously have an improved property. An improved property may be improved specific activity and/or an increased temperature sensitivity as compared to a polypeptide not comprising a amino acid substitution as defined herein, or any other improved property, for instance desirable in in food or feed processing. Advantageously a polypeptide as disclosed herein has less than 70% residual activity on acetyl-AlaAlaPro-paranitroaniline (Ac-AAP-pNA) as a substrate when the polypeptide has been kept at a temperature of 65° C. for 15 min.

Polypeptides of the invention may be obtained by several procedures known to a skilled person in the art, such as:

1. Error prone PCR to introduce random mutations, followed by a screening of obtained (variant) polypeptides and isolating of (variant) polypeptide(s) with improved properties
2. Family shuffling of related variants of the genes encoding the polypeptide according to the invention, followed by a screening of obtained variants and isolating of variants with improved properties Variants of genes encoding a polypeptide of the present invention leading to an increased level of mRNA and/or protein, resulting in more activity may be obtained by modifying the polynucleotide sequences of said genes. Among such modifications are included:

1. Improving the codon usage in such a way that the codons are (optimally) adapted to the parent microbial host.
2. Improving the codon pair usage in such a way that the codons are (optimally) adapted to the parent microbial host
3. Addition of stabilizing sequences to the genomic information encoding a polypeptide according to the invention resulting in mRNA molecules with an increased half life Methods to isolate variants with improved catalytic properties or increased levels of mRNA or protein are described in WO03/010183 and WO03/01311. Methods to optimize the codon usage in parent microbial strains are for instance described in WO2008/000632. Methods for the addition of stabilizing elements to the genes encoding the polypeptide of the invention are described in WO2005/059149.

Accordingly, in one aspect, the invention provides a method of generating a variant polypeptide, wherein the method comprises i. selecting a parent polypeptide comprising at least 60%, 70%, 75%, 80%, 85%, 90%, 91%, 92%, 93%, 94%, 95%, 96%, 97%, 98%, 99% or 100% identity to the amino acid sequence according to SEQ ID NO: 1, or to a mature polypeptide of SEQ ID NO: 1; and, ii. substituting at least one combination of amino acids resulting in a combination of amino acids selected from the group consisting of (Glu (E) at position 238, Val (V) at position, Ala (A) at position 460), (Ser (S) at position 279, Val (V) at position 242, Ile (I) at position 507), (Thr (T) at position 145, Met (M) at position 424), (Ala (A) at position 359, Ser (S) at position 379), (Ile (I) at position 170, Thr (T) at position 421), (Ser (S) at position 441, Ser (S) at position 484), (His (H) at position 470, Arg (R) at position 288), (His (H) at position 470, Gly (G) at position 387), (Ser (S) at position 281, Ile (I) at position 373), (Ala at position 304, Ala at position 469), and (Thr (T) at position 466, Gln (Q) at position 469), and optionally at least one further amino acid of Phe (F) at position 204, Asp (N) at position 205 or Ala (A) at position 477, wherein the polypeptide does not comprise amino acid Phe (F) at position 204, when the polypeptide comprises the amino acids Glu (E) at position 238, Val (V) at position 204, and Ala (A) at position 460, wherein the positions are defined with reference to SEQ ID NO: 1; and iii. generating the variant polypeptide,
wherein, optionally, the variant polypeptide has less than 70% residual activity using Ac-AAP-pNa as a substrate after the polypeptide has been kept at a temperature of 65° C. for 15 min.

Generating a variant polypeptide as disclosed herein may include expressing a gene encoding the variant polypeptide in a suitable (recombinant) host cell, and cultivating the host cell to generate the variant polypeptide.

In another aspect the present invention provides a composition comprising a polypeptide as disclosed herein.

A composition as disclosed herein, may comprise a carrier, an excipient, an auxiliary enzyme, or other compounds. Typically a composition, or a formulation, comprises a compound with which a proline-specific endoprotease may be formulated. An excipient as used herein is an inactive substance formulated alongside with a polypeptide as disclosed herein, for instance sucrose or lactose, glycerol, sorbitol or sodium chloride. A composition comprising a polypeptide as disclosed herein may be a liquid composition or a solid composition. A liquid composition usually comprises water. When formulated as a liquid composition, the composition usually comprises components that lower the water activity, such as glycerol, sorbitol or sodium chloride (NaCl). A solid composition comprising a polypeptide as disclosed herein may comprise a granulate comprising the enzyme or the composition comprises an encapsulated polypeptide in liquid matrices like liposomes or gels like alginate or carrageenans. There are many techniques known in the art to encapsulate or granulate a polypeptide or enzyme (see for instance G. M. H. Meesters, "Encapsulation of Enzymes and Peptides", Chapter 9, in N. J. Zuidam and V. A. Nedović (eds.) "Encapsulation Technologies for Active Food Ingredients and food processing" 2010).

A composition as disclosed herein may also comprise a carrier comprising a polypeptide as disclosed herein. A polypeptide as disclosed herein may be bound or immobilized to a carrier by known technologies in the art.

The present invention also relates to a packaging, such as a can, a keg or a barrel comprising a polypeptide or a composition comprising a polypeptide as disclosed herein.

The present invention also relates to a process for preparing a composition comprising a polypeptide as disclosed herein, which may comprise spray drying a fermentation medium comprising the polypeptide, or granulating, or encapsulating a polypeptide as disclosed herein, and preparing the composition.

In another aspect the present invention relates to a nucleic acid encoding a proline-specific endoprotease, which has at least 60%, 70%, 75%, 80%, 85%, 90%, 95%, 96%, 97%, 98%, or 99% sequence identity to SEQ ID NO: 2, or to a mature coding sequence of SEQ ID NO: 2, wherein SEQ ID NO: 2 comprises at least one mutation encoding at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), (T281S, L373I), (P304A, P469A), and (P466T, P469Q), and optionally at least one further amino acid substitution I204F, Y205N or P477A, wherein the polypeptide does not comprise the amino acid substitution I204F when the polypeptide has the amino acid substitutions K238E, I204V, and V460A, wherein the amino acid substitutions are defined with reference to SEQ ID NO: 1.

In another embodiment, a nucleic acid molecule of the invention comprises a nucleic acid molecule which is the reverse complement of the nucleotide sequence shown in SEQ ID NO: 2, or the reverse complement of the mature coding sequence of SEQ ID NO: 2, comprising at least one mutation encoding at least one combination of amino acid substitutions as defined above, or a variant of either such nucleotide sequence.

Also disclosed is a nucleic acid that hybridizes under medium stringency, preferably under high stringency conditions to the complementary strand of the mature polypeptide coding sequence of SEQ ID NO:2, comprising at least one mutation encoding at least one combination of amino acid substitutions as defined above.

A nucleic acid molecule which is complementary to another nucleotide sequence is one which is sufficiently complementary to the other nucleotide sequence such that it can hybridize to the other nucleotide sequence thereby forming a stable duplex. The term "cDNA" (complementary DNA) is defined herein as a DNA molecule which can be prepared by reverse transcription from a mRNA molecule. In prokaryotes the mRNA molecule is obtained from the transcription of the genomic DNA of a gene present in a cell. In eukaryotic cells genes contain both exons, i.e. coding sequences, and introns, i.e. intervening sequences located between the exons. Therefore in eukaryotic cells the initial, primary RNA obtained from transcription of the genomic DNA of a gene is processed through a series of steps before appearing as mRNA. These steps include the removal of intron sequences by a process called splicing. cDNA derived from mRNA only contains coding sequences and can be directly translated into the corresponding polypeptide product.

In one embodiment a nucleic acid is disclosed that is an isolated, substantially pure, pure, recombinant, synthetic or variant nucleic acid of the nucleic acid disclosed herein.

In another aspect, the present invention relates to an expression vector comprising a polynucleotide as disclosed herein operably linked to at least one control sequence that directs expression of the polypeptide in an expression host cell.

There are several ways of inserting a nucleic acid into a nucleic acid construct or an expression vector which are known to a skilled person in the art, see for instance Sambrook & Russell, *Molecular Cloning: A Laboratory Manual*, 3rd Ed., CSHL Press, Cold Spring Harbor, N.Y., 2001. It may be desirable to manipulate a nucleic acid encoding a polypeptide of the present invention with control sequences, such as promoter and terminator sequences.

A promoter may be any appropriate promoter sequence suitable for a eukaryotic or prokaryotic host cell, which shows transcriptional activity, including mutant, truncated, and hybrid promoters, and may be obtained from polynucleotides encoding extracellular or intracellular polypeptides either endogenous (native) or heterologous (foreign) to the cell. The promoter may be a constitutive or inducible promoter. Preferably, the promoter is an inducible promoter, for instance a starch inducible promoter. Promoters suitable in filamentous fungi are promoters which may be selected from the group, which includes but is not limited to promoters obtained from the polynucleotides encoding *A. oryzae* TAKA amylase, *Rhizomucor miehei* aspartic proteinase, *Aspergillus* gpdA promoter, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof.

Any terminator which is functional in a cell as disclosed herein may be used, which are known to a skilled person in the art. Examples of suitable terminator sequences in filamentous fungi include terminator sequences of a filamentous fungal gene, such as from *Aspergillus* genes, for instance from the gene *A. oryzae* TAKA amylase, the genes encoding *A. niger* glucoamylase (glaA), *A. nidulans* anthranilate synthase, *A. niger* alpha-glucosidase, trpC and/or *Fusarium oxysporum* trypsin-like protease.

In another aspect the present invention relates to a host cell comprising a nucleic acid construct or an expression vector as disclosed herein. A suitable host cell may be a mammalian, insect, plant, fungal, or algal cell, or a bacterial cell. A suitable host cell may be a fungal cell, for instance from the genus *Acremonium, Aspergillus, Chrysosporium, Fusarium, Myceliophthora, Penicillium, Rasamsonia, Talaromyces, Thielavia, Trichoderma, Saccaromyces, Kluyveromyces, Pichia*, for instance *Aspergillus niger, Aspergillus awamori, Aspergillus foetidus, A. oryzae, A. sojae, Talaromyces emersonii, Rasamsonia emersonii Chrysosporium lucknowense, Fusarium oxysporum, Myceliophthora thermophila, Thielavia terrestris* or *Trichoderma reesei* or, *Saccharomyces cerevisiae, Kluyveromyces lactis, Pichia pastoris*

A host cell may be a recombinant or transgenic host cell. The host cell may be genetically modified with a nucleic acid construct or expression vector as disclosed herein with standard techniques known in the art, such as electroporation, protoplast transformation or conjugation for instance as disclosed in Sambrook & Russell, *Molecular Cloning: A Laboratory Manual*, 3rd Ed., CSHL Press, Cold Spring Harbor, N.Y., 2001. A recombinant host may overexpress a polypeptide according to the present disclosure by known techniques in the art.

In one aspect the present invention relates to a process for the production of a polypeptide as disclosed herein comprising cultivating a recombinant host cell in a suitable fermentation medium under conditions conducive to the production of the polypeptide and producing the polypeptide. A skilled person in the art understands how to perform a process for the production of a polypeptide as disclosed herein depending on a host cell used, such as pH, temperature and composition of a fermentation medium. Host cells can be cultivated in shake flasks, or in fermenters having a volume of 0.5 or 1 liter or larger to 10 to 100 or more cubic metres. Cultivation may be performed aerobically or anaerobically depending on the requirements of a host cell.

Advantageously a polypeptide as disclosed herein is recovered or isolated from the fermentation medium. Recovering or isolating a polypeptide from a fermentation medium may for instance be performed by centrifugation, filtration, and/or ultrafiltration.

A polypeptide having proline-specific endoprotease activity or a composition comprising a polypeptide as disclosed herein may be used in a large variety of applications, for instance in the production of a food or feed product, such as in the production of a protein hydrolysate. Several food proteins contain highly allergenic subfractions which may be even toxic to specific individuals, such as gluten that contains prolamines with proline-rich peptide sequences. These proteins can be subjected to the new enzyme to alleviate their antigenicity or toxicity.

A group of people to which gluten is toxic are individuals suffering from Celiac Sprue. Celiac Sprue, also known as celiac disease, is an autoimmune disease of the small intestine caused by the ingestion of gluten proteins from cereals, such as alpha-gliadin from wheat, hordein from barley, secalin from rye and avenin from oats.

Accordingly, a polypeptide having proline-specific endoprotease activity or a composition comprising a polypeptide as disclosed herein may be used in the preparation of a dietary supplement or as a medicament in the treatment of a patient suffering from Celiac Sprue, or in the treatment of gluten intolerant people.

A polypeptide as disclosed herein may also be used as a processing aid to hydrolyse gluten in a food product.

Accordingly the present invention relates to a process for the preparation of a food or feed product comprising incubating an intermediate form of a food or feed product with a polypeptide or composition comprising the polypeptide as disclosed herein and preparing the food or feed product. A food product in a process as disclosed herein includes a beverage, such as beer, wine or fruit juice, or a baked product, or a dairy product, but is not limited thereto.

A food product and/or an intermediate form of a food product may comprise gluten.

It was found that a polypeptide having proline-specific endoprotease activity as disclosed herein was capable of hydrolysing the toxic epitopes in gluten into non-toxic fragments.

An intermediate form of a food product may be any suitable form of a food product during the preparation of the food product. For instance, an intermediate form of beer, may be a mash and an intermediate form of bread may be a dough or a batter.

A process for the preparation of a food product according to the present disclosure may comprise a step of pasteurizing the food product. Pasteurization usually comprises heating a food product, or an intermediate form of a food product, for instance by bringing the food product or intermediate form of a food product to a temperature of between 60 to 68° C. between 10 to 20 min, or between 12 and 18 min, or to a temperature of between 70-74° C., such as about 72° C. for at least 5, 10 or 15 seconds.

A food product in a process as disclosed herein may also be a protein hydrolysate. Accordingly, the present disclosure relates to a process for the preparation of a protein hydrolysate, comprising contacting a protein substrate with a polypeptide or a composition as disclosed herein, and producing the protein hydrolysate. A protein hydrolysate may be prepared from any suitable protein substrate, for instance a protein substrate that is rich in proline residues, such as gluten in cereals or caseins in bovine milk.

In one aspect the present invention relates to a food product obtainable by a process for the preparation of a food product as disclosed herein.

The following examples illustrate the invention.

EXAMPLES

Materials and Methods

Standard DNA procedures were carried out as described elsewhere (Sambrook &Russell, 2001, *Molecular cloning: a laboratory manual*, 3$^{rd}$ Ed., Cold Spring Harbor Laboratory Press, Cold Spring Harbor, N.Y.) unless otherwise stated. DNA sequences were ordered at DNA 2.0.

Example 1

Cloning, Expression and Recovery (Mutant) Proline-specific Endoprotease (PEP)

Example 1.1

Cloning and Expression

The protein sequence of proline-specific endoprotease (PEP) from *A. niger* is shown in SEQ ID NO: 1, wherein the first 17 amino acids are a signal sequence of pectinemethylesterase of *A. niger* (PMeA ss; SEQ ID NO: 2) and the following part comprises 19 amino acids of the prosequence of *A. niger* proline specific endoprotease (SEQ ID NO: 4).

A codon-adapted DNA sequence for expression of this protein in *Aspergillus niger* was designed containing additional restriction sites for subcloning in an *Aspergillus* expression vector. Codon adaptation was performed as described in WO 2008/000632. The codon optimized DNA sequence for *A. niger* of the gene encoding the PEP protein of SEQ ID: NO: 1 is shown in SEQ ID NO: 2.

In a similar way mutant proline-specific endoprotease of SEQ ID NO: 1, PEP13-PEP23, having the combination of amino acid substitutions as listed in Table 1, mutant proline specific endoprotease having a single mutation I204F, Y205N, or P477A, and mutant proline-specific endoprotease PEP-5_70, PEP-5_73, PEP-5_74 (Table 3) were codon optimized for expression in *Aspergillus niger*.

The translational initiation sequence of the glucoamylase glaA promoter was modified into 5'-CACCGTCAAA ATG-3' and an optimal translational termination sequence 5'-TAAA-3' was used in the generation of the expression construct (as also detailed in WO2006/077258). A DNA fragment containing a.o. part of the glucoamylase promoter and the PEP encoding gene was synthesized completely, purified and digested with EcoRI and PacI. The pGBTOP-16 vector (FIG. 1) was linearized by EcoRI/PacI digestion and the linearized vector fragment was subsequently purified by gel-extraction. The DNA fragment containing the PEP coding region was cloned into the pGBTOP-16 vector resulting in pGBTOP-PEP. Subsequently, *A. niger* GBA 306 (ΔglaA, ΔpepA, ΔhdfA, adapted BamHI amplicon, ΔamyBII, ΔamyBI, ΔamyA alpha-amylase and glucoamylase negative strain) was transformed with linearized pGBTOP-PEP vector by Nott-digestion, in a co-transformation protocol with linearized pGBAAS-4, with strain and methods as described in WO 2011/009700 and references therein, and selected on acetamide containing media and colony purified according to standard procedures. Transformation and selection is performed as described in WO 98/46772 and WO 99/32617. Strains containing the PEP gene were selected via PCR with primers specific for the PEP gene to verify presence of the pGBTOP-PEP expression cassette. Transformants were selected, named PEP13-PEP23, I204F, Y205N, P477A and EDP-5_70, EDP-5_73, EDP-5_74, and further replicaplated to obtain a single strain inoculum.

Example 1.2

Production of (Mutant) PEP in *A. niger* PEP Strain

For each (mutant) proline-specific endoprotease PEP of Example 1.1, fresh *A. niger* PEP spores were prepared. 4 shake flasks with 100 ml fermentation medium 1 (10% w/v Corn Steep Solids, 1% w/v glucose.H$_2$O, 0.1% w/v NaH$_2$PO$_4$.H$_2$O, 0.05% w/v MgSO$_4$.7H$_2$O, 0.025% w/v Basildon, pH 5.8) in 500 ml shake flasks with baffle were inoculated with 10$^7$ spores. These pre-cultures were incubated at 34° C. and 170 rpm for 16-24 hours. From the pre-cultures, 50 ml was used for inoculation of 1 shake flasks with 1 liter Fermentation medium 2 (15% w/v maltose, 6% w/v bacto-soytone, 1.5% w/v (NH$_4$)$_2$SO$_4$, 0.1% w/v NaH$_2$PO$_4$.H$_2$O, 0.1% w/v MgSO$_4$.7H$_2$O, 0.1% w/v L-arginine, 8% w/v Tween-80, 2% w/v Basildon, 2% w/v MES pH 5.1) in a 5 liter shake flask size and shaken at 34° C. and 170 rpm. After 3, 4, 5, and 6 days incubation the pH of the culture was lowered to pH 5.0 using 2 N HCl and samples from each of these time points were analysed for PEP activity. 50 mL samples were taken and the supernatant was separated from the biomass by centrifugation and subsequent filtering. The sample with the highest activity was used to characterize the PEP mutant produced.

Example 2

Proline-specific Endoprotease (PEP) Activity Measurements

100 µL of culture supernatant as produced in Example 1, diluted in 0.1 M sodium acetate buffer at pH4.5 with 50 mM NaCl, was incubated with 100 µL 6 mM Ac-AAP-pNA (acetyl-AlaAlaPro-paranitroaniline from Selleckchem or CPC Scientific; purity>95.0% based on HPLC analysis) in 0.1 M NaAc buffer at pH4.5 with 50 mM NaCl, in a Nunc 96 well flat bottom MTP (micro-titer plate). After 60 minutes at 20° C. the reaction was stopped by adding 40 µL of 1 M HCl. The pNA which had been liberated by PEP was measured in a Tecan MTP spectrophotometer at 405 nm (A405) (www.tecan.com). The blank was prepared by mixing the diluted culture supernatant with the substrate solution which had been mixed with the HCl solution beforehand. The activity is expressed in pNASU's.

1pNASU is the amount of enzyme which liberates from Ac-AAP-pNA in 1 hour the amount of pNA that corresponds to an increase in absorption at 405 nm of 1 OD, using the conditions as described above. The A405 should not be below the blank value at the start of the reaction, or above 2.5 at the end of the reaction, nor may the A405 exceed the linear range of the spectrophotometer that is used.

Example 3

Thermal Stability Proline-specific Endoprotease

To assess the thermal stability of parent PEP and the mutants PEP13-PEP23 the activity assay was preceded by an incubation of 100 µL aliquots of a tenfold dilution of the culture supernatant produced in Example 1 in buffer (0.1 M NaAc pH 4.5, with 50 mM NaCl) at 55° C. and 65° C. for 15 min in a PCR plate in a PCR machine. After the 15 min incubation the samples were rapidly cooled to 25° C. in the PCR machine. The pNASU/mL of every sample was measured. The initial activity measured before incubation at elevated temperature (0 minutes) was used as reference (100%) to determine the residual activity. All activities were measured four times.

Table 1 shows that all mutant proline-specific endoproteases have a significant reduced residual activity as compared to the parent proline-specific endoprotease after keeping the enzymes at 65° C. and 60° C. for 15 min.

TABLE 1

Residual activity of proline-specific endoprotease mutants PEP13-PEP23 compared to the parent proline-specific endoprotease.

| Clone | Substitutions with respect to parent SEQ ID NO: 1 | Residual activity (pNASU) at indicated T after 15' | | |
|---|---|---|---|---|
| | | 55° C. | 60° C. | 65° C. |
| PEP | Parent | 100% | 93% | 80% |
| PEP13 | K238E + I204V + V460A | 61% | 14% | 0% |
| PEP14 | F279S + A242V + N507I | 86% | 40% | 1% |
| PEP15 | T145A + K424M | 99% | 63% | 9% |
| PEP16 | T359A + F379S | 96% | 55% | 0% |
| PEP17 | M170I + A421T | 88% | 53% | 4% |
| PEP18 | N441S + G484S | 92% | 50% | 3% |
| PEP19 | L470H + Q288R | 92% | 48% | 5% |
| PEP20 | L470H + E387G | 89% | 37% | 1% |
| PEP21 | T281S + L373I | 64% | 59% | 14% |
| PEP22 | P304A + P469A | 95% | 77% | 5% |
| PEP23 | P466T + P469Q | 93% | 40% | 0% |

Example 4

Additional Mutation to Further Reduce Thermostability in Proline-specific Endoproteases The mutant proline-specific endoproteases PEP 20 having substitutions L470H+E387G and PEP 23, having substitutions P466T+P469Q from Table 1 were further combined with the single mutations Y205N and either P477A or I204F, respectively. Cloning, expression and recovery of the single and triple mutants was performed as described in Example 1. To assess the thermal stability of the single and triple mutants the activity assay was preceded by an incubation of 100 µL aliquots of a tenfold dilution of the culture supernatant in buffer (0.1 M NaAc pH 4.5, with 50 mM NaCl) in a PCR plate in a PCR machine at the temperatures as indicated in Table 2 and 3. After the 15 min incubation the samples were rapidly cooled to 25° C. The pNASU/mL of every sample was measured. The initial activity measured at the start of the incubation was used as reference (100%) to determine the residual activity.

The thermostability of proline-specific endoprotease of *Aspergillus niger* containing the single mutations Y205N, P477A or I204F and containing triple mutations are shown in Table 2 and 3 below.

TABLE 2

Residual activity of mutant proline-specific endoproteases of *Aspergillus niger* containing a single substitution

| Substitutions with respect to parent SEQ ID NO: 1 | Residual activity (pNASU) at indicated T after 15' | | | | | |
|---|---|---|---|---|---|---|
| | 66.5° C. | 63.3° C. | 58.6° C. | 53.0° C. | 48.5° C. | 45.4° C. |
| I204F | 0.0% | 4.4% | 53.7% | 86.4% | 123.2% | 130.5% |
| Y205N | 0.3% | 5.0% | 42.2% | 83.1% | 101.3% | 117.4% |
| P477A | 0.4% | 0.6% | 25.6% | 84.1% | 108.8% | 125.7% |

TABLE 3

Residual activity of triple mutants of proline-specific endoprotease of Aspergillus niger

| Substitutions with respect to parent SEQ ID NO 1 | Residual activity (pNASU) at indicated T after 15' | | | | | |
|---|---|---|---|---|---|---|
| | 60.4° C. | 57.3° C. | 52.5° C. | 47.0° C. | 42.4° C. | 39.4° C. |
| PEP-5_70 L470H + E387G + Y205N | 0% | 1% | 5% | 52% | 90% | 99% |
| PEP-5_73 P466T + P469Q + I204F | 1% | 1% | 12% | 66% | 91% | 98% |
| PEP-5_74 P466T + P469Q + P477A | 0% | 0% | 3% | 46% | 80% | 96% |

The results show that the thermostability of mutant proline-specific endoprotease PEP20 and PEP23 can be further reduced by further amino acid substitutions such as by introduction of the amino acid substitutions I204F, Y205, or P477A.

Example 5

Substrate Specificity Proline-specific Endoproteases

To confirm that the mutants PEP13 to PEP23 are proline-specific endoproteases, the substrate specificity of the different PEP mutants PEP13-PEP23 was assessed using cytochrome c form horse heart. Dilutions of the culture supernatant prepared in Example 1 are incubated with cytochrome c from horse heart (Sigma) which has the amino acid sequence of SEQ ID NO: 3. The substrate was prepared by dissolving 1 mg/mL cytochrome c in 100 mM sodium acetate buffer, pH 4.5 and heating at 95° C. for 15 min. The culture supernatant is diluted in 100 mM NaAc buffer pH 4.5 and incubated with the cytochrome c substrate solution at 50° C. for 3 hours. The reaction is stopped by dilution in water and addition of 0.4M NaOH to raise to pH to 10. The incubated reaction mixtures are analysed on an Accela UHPLC (Thermo Electron, Breda, The Netherlands) coupled to a LTQ-Orbitrap Fourier Transform Mass Spectrometer (Thermo Electron, Bremen, Germany). The chromatographic separation was achieved with a 2.1×50 mm 1.8 µm particle size, 80 Å pore size, C-18 Eclipse XDB Zorbax column (Agilent Santa Clara, Calif., USA), using a gradient elution with (A) LC-MS grade water containing 0.1% formic acid and (B) LC-MS grade acetonitrile containing 0.1% formic acid solution (Biosolve BV, the Netherlands) as mobile phases. The 25 min gradient is started from 0%, kept there for 1 minute and then linearly increased to 40% (B) in 14 min, then washing with 80% (B) for 4 min and re-equilibrating with 0% (B) for 5 min. The flow rate is kept at 0.4 ml/min, using an injection volume of 5 µl and the column temperature was 50° C. The mass spectrometry data acquisition is accomplished with Top 3 data-dependent acquisition using "Chromatography" and "Dynamic exclusion" options in which only and charge states 2 and 3 were included. Resolution for the FT MS scan was 15000 and scanned for m/z range 210-2000, whereas the MS/MS experiments were performed in the ion trap. The isolation width is set at 3.0 m/z, and the normalised collision energy was set to 35. Peptide identification is performed using accurate mass and MS/MS de novo sequenced data.

When the major peptides SEQ ID NO: 4 to SEQ ID NO: 8, in particular SEQ ID NO: 4 to SEQ ID NO: 6, are formed, this shows that the mutant proline-specific endoproteases have proline-specific endoprotease activity, i.e. have a preference to cut at a position where there is a proline residue in the peptide.

The invention claimed is:

1. A polypeptide having proline-specific endoprotease activity, wherein the polypeptide is selected form the group consisting of:
   i. a polypeptide comprising the amino acid sequence of SEQ ID NO:1, wherein the polypeptide further comprises at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), and (T281S, L373I), wherein the positions are defined with reference to SEQ ID NO:1;
   ii. a polypeptide according to i), but lacking a signal sequence and/or a proprotein sequence;
   iii. a polypeptide according to i) or ii), wherein the polypeptide has at least 90% sequence identity to the amino acid sequence of SEQ ID NO:1; and
   iv. a polypeptide encoded by a nucleic acid which has at least 90% sequence identity to SEQ ID NO:2, or to a mature coding sequence of SEQ ID NO:2, wherein SEQ ID NO:2 comprises at least one mutation encoding at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), and (T281S, L373I), wherein the amino acid substitutions are defined with reference to SEQ ID NO:1.

2. The polypeptide of claim 1, wherein the polypeptide has less than 70% residual activity on acetyl-AlaAlaPro-paranitroaniline (Ac-AAP-pNA) as a substrate after the polypeptide has been kept at a temperature of 65° C. for 15 min.

3. The polypeptide of claim 2, wherein said polypeptide is isolated, substantially pure, pure, recombinant, synthetic, or variant.

4. A method for generating a variant polypeptide, wherein the method comprises:
   i. selecting a parent polypeptide comprising at least 90% sequence identity to the amino acid sequence according to SEQ ID NO:1, or to a mature polypeptide of SEQ ID NO:1; and,
   ii. providing at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), and (T281S, L373I), wherein the positions are defined with reference to SEQ ID NO:1; and
   iii. generating the variant polypeptide.

5. A composition comprising the polypeptide according to claim 2.

6. The composition according to claim 5, comprising a carrier, an excipient, or an auxiliary enzyme.

7. A nucleic acid encoding a proline-specific endoprotease, which has at least 90% sequence identity to SEQ ID NO:2, or to a mature coding sequence of SEQ ID NO:2, wherein SEQ ID NO:2 comprises at least one mutation encoding at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), and (T281S, L373I), and optionally one further amino acid substitution I204F, Y205N or P477A, wherein the polypeptide does not comprise the amino acid substitution I204F when the polypeptide has the amino acid substitutions K238E, I204V, and V460A, wherein the amino acid substitutions are defined with reference to SEQ ID NO:1.

8. A nucleic acid that is an isolated, substantially pure, pure, recombinant, synthetic or variant nucleic acid of the nucleic acid of claim 7.

9. An expression vector comprising the nucleic acid according to claim 7 operably linked to at least one control sequence that direct expression of the polypeptide in a host cell.

10. A recombinant host cell comprising the nucleic acid according to claim 7, or an expression vector thereof.

11. A method for the preparation of the polypeptide according to claim 2, comprising cultivating a host cell in a suitable fermentation medium, under conditions that allow expression of the polypeptide, and preparing the polypeptide, and optionally further comprising recovering the polypeptide.

12. A process for the preparation of a food or feed product comprising bringing an intermediate form of a food or feed product into contact with the polypeptide according to claim 2, or a composition thereof, and preparing the food or feed product.

13. The process according to claim 12, wherein the food product is a beverage, optionally a beer.

14. The process according to claim 12, wherein the food product comprises gluten.

15. The polypeptide of claim 1, wherein said polypeptide according to i) or iv) further comprises at least one amino acid substitution selected from the group consisting of I204F, Y205N and P477A, wherein the amino acid substitution I204F is not present in a polypeptide having the amino acid substitutions K238E, I204V, and V460A, and wherein the substitutions are defined with reference to SEQ ID NO:1.

16. The method of claim 4, wherein at least one further amino acid substitution selected from the group consisting of I204F, Y205N and P477A is provided, wherein the amino acid substitution I204F is not present in a polypeptide having the amino acid substitutions K238E, I204V, and V460A, and wherein the substitutions are defined with reference to SEQ ID NO:1.

17. The method of claim 4, wherein the variant polypeptide has less than 70% residual activity on acetyl-AlaAlaPro-paranitroaniline (Ac-AAP-pNA) as a substrate after the polypeptide has been kept at a temperature of 65° C. for 15 min.

18. The polypeptide of claim 1, wherein the polypeptide is selected form the group consisting of:
  i. a polypeptide comprising the amino acid sequence of SEQ ID NO:1, wherein the polypeptide further comprises at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), and (T281S, L373I), wherein the positions are defined with reference to SEQ ID NO:1;
  ii. a polypeptide according to i), but lacking a signal sequence and/or a proprotein sequence;
  iii. a polypeptide according to i) or ii), wherein the polypeptide has at least 95% sequence identity to the amino acid sequence of SEQ ID NO:1; and
  iv. a polypeptide encoded by a nucleic acid which has at least 95% sequence identity to SEQ ID NO:2, or to a mature coding sequence of SEQ ID NO:2, wherein SEQ ID NO:2 comprises at least one mutation encoding at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), and (T281S, L373I), wherein the amino acid substitutions are defined with reference to SEQ ID NO:1.

19. The polypeptide of claim 1, wherein the polypeptide is selected form the group consisting of:
  i. a polypeptide comprising the amino acid sequence of SEQ ID NO:1, wherein the polypeptide further comprises at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), and (T281S, L373I), wherein the positions are defined with reference to SEQ ID NO:1;
  ii. a polypeptide according to i), but lacking a signal sequence and/or a proprotein sequence;
  iii. a polypeptide according to i) or ii), wherein the polypeptide has at least 97% sequence identity to the amino acid sequence of SEQ ID NO:1; and
  iv. a polypeptide encoded by a nucleic acid which has at least 97% sequence identity to SEQ ID NO:2, or to a mature coding sequence of SEQ ID NO:2, wherein SEQ ID NO:2 comprises at least one mutation encoding at least one combination of amino acid substitutions selected from the group consisting of (K238E, I204V, V460A), (F279S, A242V, N507I), (T145A, K424M), (T359A, F379S), (M170I, A421T), (N441S, G484S), (L470H, Q288R), (L470H, E387G), and (T281S, L373I), wherein the amino acid substitutions are defined with reference to SEQ ID NO:1.

* * * * *